United States Patent
Ogura et al.

(10) Patent No.: US 7,625,748 B2
(45) Date of Patent: Dec. 1, 2009

(54) FLOW CELL DEVICE, SENSOR UNIT AND ASSAY APPARATUS

(75) Inventors: Nobuhiko Ogura, Kanagawa (JP); Hitoshi Shimizu, Kanagawa (JP); Tatsuo Fujikura, Kanagawa (JP); Koji Kuruma, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 270 days.

(21) Appl. No.: 11/475,064

(22) Filed: Jun. 27, 2006

(65) Prior Publication Data
US 2007/0004030 A1 Jan. 4, 2007

(30) Foreign Application Priority Data
Jun. 29, 2005 (JP) .............................. 2005-190770

(51) Int. Cl.
C12M 3/00 (2006.01)
C12M 1/34 (2006.01)
(52) U.S. Cl. .................. 435/288.5; 435/7.1; 435/283.1; 435/287.1; 435/287.2; 435/288.3; 435/288.4; 436/524; 436/525; 436/527; 422/50; 422/58; 422/68.1
(58) Field of Classification Search .................. 435/7.1, 435/283.1, 287.1, 287.2, 288.3, 288.4, 288.5; 422/50, 58, 68.1; 436/524, 525, 527
See application file for complete search history.

(56) References Cited

U.S. PATENT DOCUMENTS

| | | | |
|---|---|---|---|
| 4,834,946 A * | 5/1989 | Levin | .......................... 422/101 |
| 5,164,589 A | 11/1992 | Sjodin | |
| 5,313,264 A | 5/1994 | Ivarsson | |
| 5,991,048 A | 11/1999 | Karlson et al. | |
| 6,192,168 B1 * | 2/2001 | Feldstein et al. | .............. 385/12 |
| 6,303,389 B1 * | 10/2001 | Levin et al. | .................. 436/518 |
| 6,346,376 B1 * | 2/2002 | Sigrist et al. | .................... 435/5 |
| 6,350,413 B1 | 2/2002 | Reichert et al. | |
| 6,361,958 B1 * | 3/2002 | Shieh et al. | .................. 435/7.1 |
| 2004/0175734 A1 | 9/2004 | Stahler et al. | |

FOREIGN PATENT DOCUMENTS

| | | |
|---|---|---|
| EP | 1 512 961 A | 3/2005 |
| WO | WO 97/01087 A | 1/1997 |
| WO | WO 03002985 A | 9/2003 |

* cited by examiner

*Primary Examiner*—Melanie Yu
(74) *Attorney, Agent, or Firm*—Sughrue Mion, PLLC (57) ABSTRACT

A flow cell device is incorporated in the sensor unit for surface plasmon resonance (SPR) assay. A box shaped flow cell body has a lower surface, and is disposed in contact of the lower surface with a sensing surface for detecting reaction of sample. Two flow channels are formed in the flow cell body, for flow of the sample. Each of the flow channels include a fluid passageway, formed in the lower surface, for flow of the sample in contact with the sensing surface. Two end cavities are formed in an upper surface of the flow cell body and open therein, to extend from ends of the fluid passageway. The flow channels are arranged adjacent to one another, disposed to extend in a direction of the flow. Fluid passageways of the flow channels are overlapped partially on one another in a flow cell longitudinal direction of the flow cell body.

18 Claims, 8 Drawing Sheets

FIG. 11

FLOW CELL DEVICE, SENSOR UNIT AND ASSAY APPARATUS

BACKGROUND OF THE INVENTION

1. Field of the Invention

The present invention relates to a flow cell device, sensor unit and assay apparatus. More particularly, the present invention relates to a flow cell device, sensor unit and assay apparatus in which non-specific adsorption can be prevented in a rapid assay.

2. Description of the Related Art

An assay apparatus for assay in utilizing attenuated total reflection is used for various kinds of studies in a biochemical field or the like, for example to study interaction of protein, DNA and various biomaterials, and to select candidate drugs by screening. Also, the technique is useful in the fields of the clinical medicine, food industries and the like.

A surface plasmon resonance (SPR) sensor is known as an assay apparatus in utilizing attenuated total reflection. Surface plasmon is a term to mean the compressional wave created on the surface of the metal and included in plasmon as quantized expression of the compressional wave. Free electrons in a metal vibrate to generate the compressional wave.

U.S. Pat. Nos. 5,164,589 and 5,313,264 (corresponding to JP-B 3294605) disclose the SPR assay apparatus with Kretschmann configuration. In the assay apparatus, the sensing surface is positioned opposite to an interface where a metal thin film is connected with a dielectric block. The sensing surface is caused to create surface plasmon resonance. Reaction of samples is assayed by detecting the SPR on the sensing surface. Then total reflection of the illuminating light occurs.

Upon the total reflection created on the metal/dielectric interface, a small component of the light passes through the metal film without reflection, and penetrates to the sensing surface. A wave of the penetrating component is called an evanescent wave. Surface plasmon resonance (SPR) is created when frequency of the evanescent wave coincides with that of the surface plasmon. In response to this, intensity of the reflected light attenuates remarkably. In the assay apparatus, the attenuation in the reflected light reflected by the metal/dielectric interface is detected, to recognize creation of the SPR on the sensing surface.

A sample or biomaterial, such as protein, is handled as sample fluid for the purpose of preventing deactivation or modification due to drying. The sample fluid contains biomaterial and fluid medium, examples of which include pure water, physiological saline water, liquid buffer and the like. U.S. Pat. Nos. 5,164,589 and 5,313,264 (corresponding to JP-B 3294605), for assay of reaction of a sample or biomaterial, suggest a use of a flow channel which is positioned on a sensing surface and where a sample fluid flows. A linker film is formed on the sensing surface for immobilizing ligand or sample. Ligand fluid is introduced in the flow channel, to immobilize the ligand on the linker film. After this, analyte fluid is introduced for causing the ligand to contact the analyte, to assay the interaction between the ligand and analyte.

A body of the assay apparatus has an assay stage. A sensor unit of a chip type includes a glass substrate and a thin film of metal formed thereon, and is placed on the assay stage for assay. Tubes or conduits are connected with pumps, valves and the like, to cause the sample fluid to flow from a reservoir directly to the flow channel. However, there is a problem in risk of contamination caused by mixing of residual sample in the conduits with the sample fluid.

A suggested SPR assay apparatus includes pipette devices each of which has a pipette tip and a pipette head. The pipette tip has a partially conical surface, and has an end opening. The pipette head is connected with and supports the pipette tip in a removable manner. The sample fluid or other liquids are introduced from a reservoir to the flow channel of the sensor unit. The pipette tip is detipped for renewal at each time of a change of the liquids, so a contamination of the liquids is prevented in introduction to the flow channel.

A sensor unit is used in the SPR assay apparatus. The sensor unit includes a flow cell device, a prism and a sealing structure. The flow cell device has a flow channel. The prism is overlaid with a thin film of metal. The sealing structure keeps a lower surface of the flow cell device secured to an upper surface of the prism or keeps the flow channel positioned on the thin film. A linker film is formed on the thin film of the sensor unit as described above. Pipette devices are used for introducing fluid into the flow channel for assay, the fluid being one of ligand fluid, analyte fluid and the like.

There are regions on the linker film, which are a measuring region having bindable groups for ligand, and a reference region after deactivation of the bindable groups. A light source is driven to apply light to the measuring region and the reference region. Reflected light from those are photoelectrically converted by a photo detector, to output a measuring signal and a reference signal. The signals are arithmetically processed to obtain a difference, ratio or the like and are analyzed. So a result of high precision can be obtained after canceling electrical noise due to individual specificity of the sensor unit and changes in the temperature of fluids. Influence of non-specific adsorption is suppressed by the analysis, the non-specific adsorption be in a problem of unwanted binding of sample on the linker film in a biochemical sample, such as protein, DNA and the like.

However, a difference is likely to occur in the amount of the non-specific adsorption between the measuring region with the bindable groups and the reference region without the bindable groups, due to the difference in the characteristic of the surface. The difference in the amount to the non-specific adsorption cannot be eliminated even after precise analysis.

To introduce ligand fluid to contact only the measuring region, two or more of the flow channel should be formed and used. This may be effective in suppressing a difference between amounts of the non-specific adsorption without deactivating the bindable groups of the measuring region. However, a structure with two or more of the flow channel will enlarge the size of the sensor unit. For improvement in the SPR assay of the sample, higher precision and higher efficiency in assay with a great number of the sample at one time are desired. However, rise in the throughput of the assay is desired, but is impossible due to an enlarge shape of the sensor unit.

SUMMARY OF THE INVENTION

In view of the foregoing problems, an object of the present invention is to provide a flow cell device, sensor unit and assay apparatus in which non-specific adsorption can be prevented in a rapid assay.

In order to achieve the above and other objects and advantages of this invention, a flow cell device is provided. A flow cell body has a lower surface, and is disposed in contact of the lower surface with a sensing surface for detecting reaction of sample. At least two flow channels are formed in the flow cell body, for flow of the sample. Each of the flow channels include a fluid passageway, formed in the lower surface, for flow of the sample in contact with the sensing surface, and two end cavities, formed in an upper surface of the flow cell body and open therein, to extend from ends of the fluid passageway. At least one flow channel set constitutes the at least two flow channels, the flow channels being arranged adjacent to one another as viewed in a direction of the flow, disposed to extend in the direction of the flow, fluid passageways of the flow channels being overlapped partially on one another in a predetermined direction of the flow cell body.

Preferably, the fluid passageway is formed to extend substantially linearly in the predetermined direction.

In one preferred embodiment, the fluid passageway extends to intersect with a reference straight line extending in the predetermined direction.

Preferably, the reference straight line is a flow cell central line defined by a shape of the flow cell body.

Preferably, a reference straight line of the flow cell body is disposed to extend in the predetermined direction. The fluid passageway is so disposed that the end cavities are disposed at an equal path length from intersection point between the straight line and the reference straight line.

Preferably, the fluid passageway is formed to extend substantially linearly.

In another preferred embodiment, the fluid passageway is formed to extend in a wave shaped bent form.

In one preferred embodiment, the fluid passageway is so disposed that a straight line that passes ends thereof extends in the predetermined direction.

Preferably, the fluid passageway includes a first section, and a second section disposed to extend from a downstream end of the first section in an inclined direction to define a bent form.

Preferably, the fluid passageway is in a bent form toward a reference straight line, and the two flow channels are opposed to one another with respect to the reference straight line.

Preferably, the fluid passageway is formed to extend in an S shaped bent form.

Preferably, the two flow channels are opposed to one another with respect to the reference straight line.

Preferably, the at least two flow channels are an even number of flow channels, and disposed in a rotationally symmetrical manner.

Furthermore, a retention portion is formed to project from the flow cell body, engageable with a support having the sensing surface, for keeping the sensing surface in contact with the lower surface.

Preferably, the flow cell body includes a hard part. An elastic flexible part is formed together with the hard part according to dual molding, having a smaller hardness than the hard part, for constituting at least an edge of the fluid passageway.

A sensor unit has a dielectric medium overlaid with a thin film for attenuating reflected illuminating light upon application of the illuminating light to satisfy a total reflection condition, and at least one flow cell device disposed to contact the dielectric medium, for causing sample to flow to a sensing surface on the thin film, wherein when the sample contacts the sensing surface, an incidence angle of the illuminating light of occurrence of attenuation is changed according to reaction of the sample. In the sensor unit, the flow cell device includes a flow cell body, having a lower surface, and disposed in contact of the lower surface with the sensing surface. At least two flow channels are formed in the flow cell body, for flow of the sample. Each of the flow channels includes a fluid passageway, formed in the lower surface, for flow of the sample in contact with the sensing surface, and two end cavities, formed in an upper surface of the flow cell body and open therein, to extend from ends of the fluid passageway. The flow cell device includes at least one flow channel set for constituting the at least two flow channels, the flow channels being arranged adjacent to one another, disposed to extend in a direction of the flow, fluid passageways of the flow channels being overlapped partially on one another in a predetermined direction of the flow cell body.

Preferably, the flow channels in the flow channel set include a first flow channel adapted to generating a measuring signal of information of detecting the reaction. A second flow channel is adapted to generating a reference signal for analysis of the measuring signal.

Preferably, the at least one flow cell device is plural flow cell devices arranged in a flow cell array.

An assay apparatus for assay in utilizing attenuated total reflection includes an assay stage for supporting a sensor unit removably, a light source for applying illuminating light to a thin film of the sensor unit to satisfy a total reflection condition, and a photo detector for receiving the illuminating light reflected by the thin film and for conversion into an electric signal. In the assay apparatus, the sensor unit has a dielectric medium overlaid with the thin film for attenuating reflected illuminating light upon application of the illuminating light to satisfy a total reflection condition, and at least one flow cell device disposed to contact the dielectric medium, for causing sample to flow to a sensing surface on the thin film, wherein when the sample contacts the sensing surface, an incidence angle of the illuminating light of occurrence of attenuation is changed according to reaction of the sample. The flow cell device includes a flow cell body, having a lower surface, and disposed in contact of the lower surface with the sensing surface. At least two flow channels are formed in the flow cell body, for flow of the sample. Each of the flow channels includes a fluid passageway, formed in the lower surface, for flow of the sample in contact with the sensing surface, and two end cavities, formed in an upper surface of the flow cell body and open therein, to extend from ends of the fluid passageway. The flow cell device includes at least one flow channel set for constituting the at least two flow channels, the flow channels being arranged adjacent to one another, disposed to extend in a direction of the flow, fluid passageways of the flow channels being overlapped partially on one another in a predetermined direction of the flow cell body.

Preferably, there are two paths where the light source applies the illuminating light to the thin film, and the illuminating light travels to a measuring point defined in the fluid passageway. The measuring point is disposed at a first path length from a first end cavity for dispensing the sample among the end cavities, the first path length being equal between the at least two flow channels.

Preferably, the measuring point is disposed at a second path length from a second end cavity for exiting the sample among the end cavities, and the second path length is equal to the first path length.

In one preferred embodiment, the measuring point is disposed at a second path length from a second end cavity for exiting the sample among the end cavities, and the second path length is greater than the first path length.

Consequently, it is possible in the flow cell device, sensor unit and assay apparatus to prevent non-specific adsorption in a rapid assay, owing to the combined use of the at least two flow channels.

BRIEF DESCRIPTION OF THE DRAWINGS

The above objects and advantages of the present invention will become more apparent from the following detailed description when read in connection with the accompanying drawings, in which.

DETAILED DESCRIPTION OF THE PREFERRED EMBODIMENT(S) OF THE PRESENT INVENTION

Figure 1:
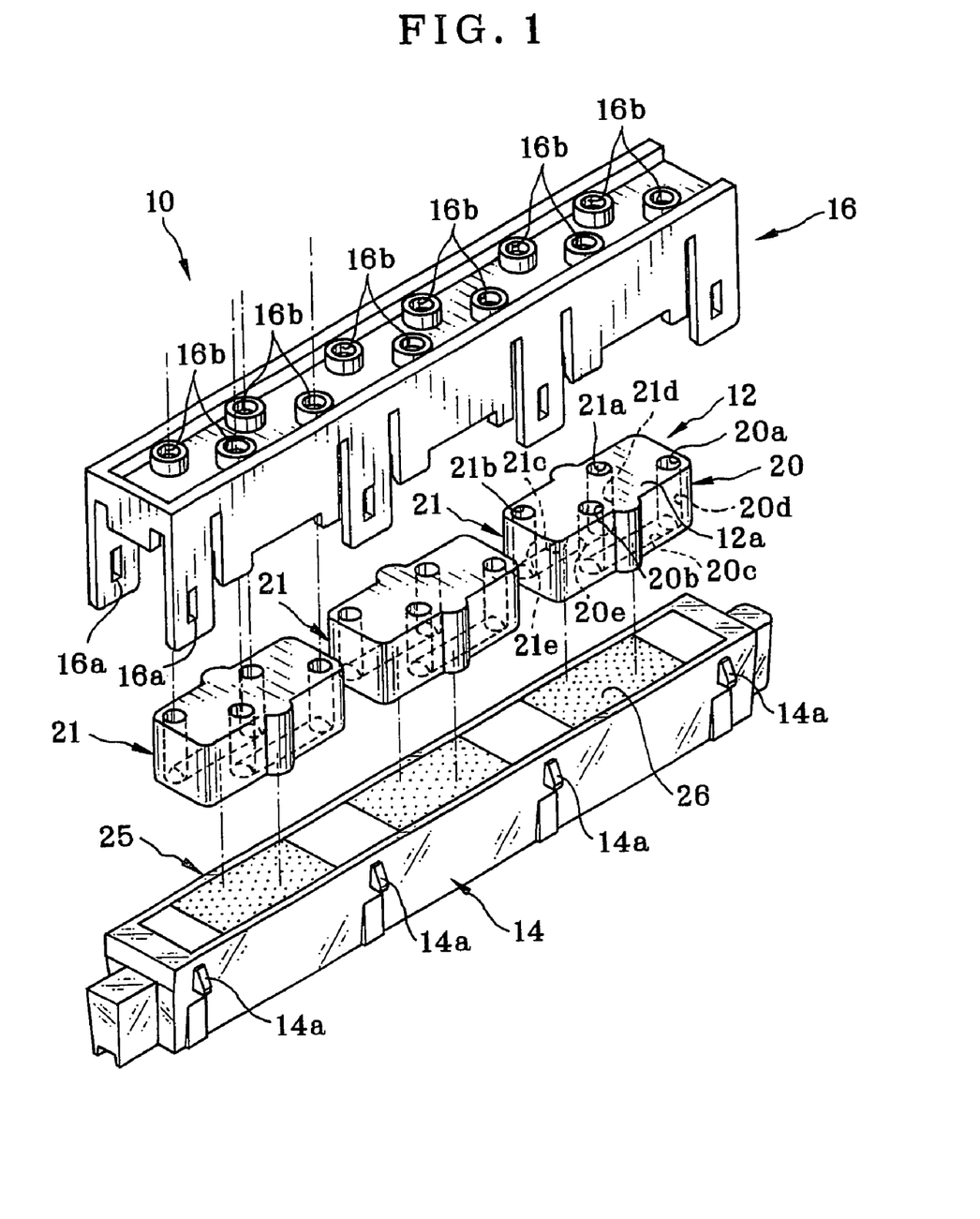
FIG. 1 is a perspective view illustrating a sensor unit for use in an assay apparatus.

In FIG. 1, a sensor unit 10 or a flow cell assembly for surface plasmon resonance (SPR) assay is illustrated. The sensor unit 10 includes three flow cell devices 12, a prism 14 as a dielectric medium, and a sealing structure 16. Each of the flow cell devices 12 has flow channels 20 and 21 as a pair. The prism 14 is overlaid with a thin film 25 of metal with a sensing surface. The sealing structure 16 connects the flow cell devices 12 to the prism 14 and keeps a lower face of the flow cell devices 12 sealed with the upper portion of the prism 14.

First and second orifices 20a and 20b are open in an upper face of the flow cell devices 12 to communicate with the flow channel 20. The flow channel 20 includes a fluid passageway 20c in a horizontally linear shape, and end cavities 20d and 20e as its ends. The fluid passageway 20c is a recess formed in a lower surface of the flow cell devices 12. The end cavity 20d extends from one end of the fluid passageway 20c to come through and define the first orifice 20a. The end cavity 20e extends from one end of the end cavities 20d to come through and define the second orifice 20b. The flow channel 21 is structurally the same as the flow channel 20, and is not described further in particular.

A flow cell body 12a in the flow cell devices 12 is a molded part in a rectangular parallelepipedic shape. The fluid passageway 20c of the flow channel 20 extends in a flow cell longitudinal direction of the flow cell body 12a. A fluid passageway 21c of the flow channel 21 extends in the same direction. One portion of the fluid passageways 20c and 21c is overlapped as viewed in the flow cell longitudinal direction. A diameter of the flow channels 20 and 21 is for example 1 mm. An interval between the first and second orifices 20a and 20b and between first and second orifices 21a and 21b is 10 mm.

Open lower portions of the fluid passageways 20c and 21c of the flow channels 20 and 21 are closed fluid-tightly with the thin film 25 by the upper surface of the prism 14 in contact with the flow cell device 12. In the flow channels 20 and 21, fluid is caused to flow in contact with the thin film 25 in the fluid passageways 20c and 21c from a first end of each of those toward a second end of the same. The flow cell device 12 is formed from elastic material for the purpose of ensuring tightness in contact with the thin film 25. Examples of elastic materials of the flow cell body 12a include rubber, polydimethylsiloxane (PDMS), and the like. When the lower surface of the flow cell body 12a is pressed on an upper surface of the prism 14, the flow cell body 12a is elastically deformed, to remove a space between its surface and the thin film 25. The number of the flow cell devices 12 is three in the sensor unit. Note that, in the sensor unit, the number of the flow cell devices 12 may not be three, but can be one or two, or four or more. Also, a longer flow cell can be used to contain plural combinations of the flow channels 20 and 21. A flow channel set as a term in the invention is constituted by the combination of the flow channels 20 and 21 in the flow cell devices 12.

The prism 14 is a transparent dielectric block, and overlaid with the thin film 25. Illuminating light is condensed by the prism 14 for application to the interface to satisfy the total reflection condition. The thin film 25 is formed in regions of plural strips by vapor deposition or other suitable methods, and opposed to the inside of the flow channels 20 and 21 formed in the flow cell devices 12. An example of material for the thin film 25 is gold (Au), silver (Ag) or the like. A thickness of the thin film 25 is 50 nm. The thickness can be changed for the suitability in view of the material of the thin film 25, a wavelength of light to be applied, and the like.

Three regions are defined where an immobilizing linker film 26 is overlaid on the thin film 25 at the center of the sensing surface. The linker film 26 is formed on the thin film 25, has reaction groups for binding and immobilizing ligand, and is a region to assay interaction between the immobilized ligand and analyte. The linker film 26 is previously produced in the course of manufacturing the sensor unit 10. An example of material for the linker film is carboxy methyl dextran. As the linker film 26 is a basis for immobilizing the ligand, various materials are available for selective use according to the type of the ligand to be immobilized. In the embodiment, three regions of the linker film 26 are formed. However, a single region of the linker film 26 may be formed to cover the entirety of the thin film 25.

The reference signal or ref-signal is an output of the SPR derived from the reference region on the linker film 26 and free from immobilization of a ligand, and is a basis of comparison with a measuring signal. The measuring signal or act-signal is an output of the SPR derived from the measuring region on the linker film 26 and for immobilization of a ligand to react with an analyte. The data analyzer effects data analysis by obtaining a data of a finite difference between the act-signal and ref-signal, and analyzes various items according to the finite difference. This makes it possible to cancel electric noise caused by external irregularities, such as individual specificity of the sensor unit 10 or the linker film 26, temperature changes of the liquid, and the like. The flow channels 20 and 21 in the flow cell devices 12 are for the purpose of the correction. One of those is for producing a measuring signal. A second of those is for producing a reference signal. In the embodiment, the flow channel 20 is for the measurement. The flow channel 21 is for the reference.

Retention claws 14a are formed on the prism 14 to protrude from side surfaces of the prism 14. Retention portions 16a of the sealing structure 16 are engageable with the retention claws 14a. The flow cell devices 12 is kept sandwiched between the sealing structure 16 and the prism 14 by engagement of the retention claws 14a and the retention portions 16a, to keep a lower surface of the flow cell devices 12 in tight contact with an upper surface of the prism 14. Thus, the sensor unit 10 is constructed as a unit having the flow cell devices 12, the prism 14 and the sealing structure 16.

Various materials can be used for forming the prism 14, their examples including optical glasses, such as borosilicate crown (BK7) glass, barium crown (Bak4) glass, and the like; and optical plastic materials, such as polymethyl methacrylate (PMMA), polycarbonate (PC), amorphous polyolefin (APO) and the like.

Figure 2:
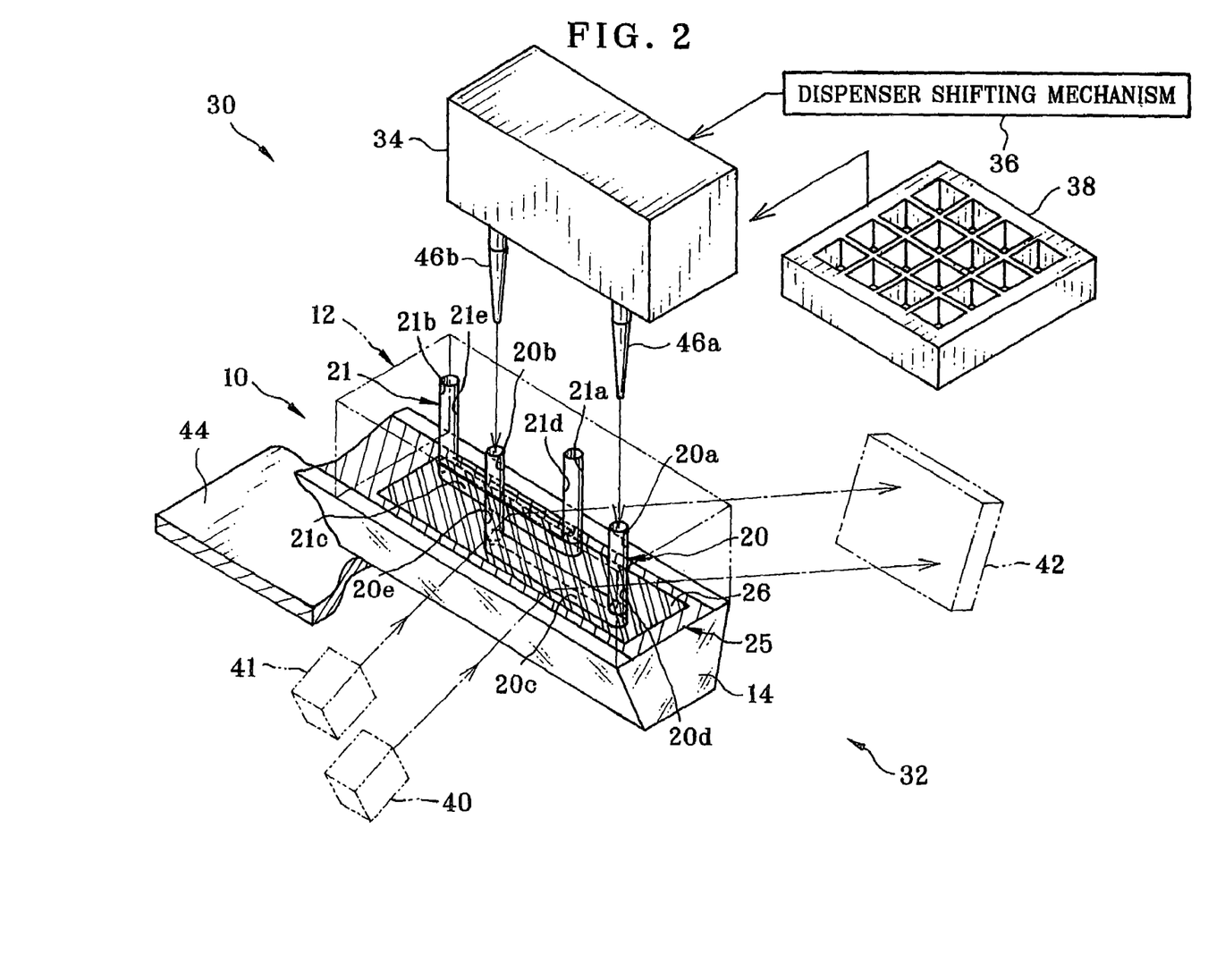
FIG. 2 is a perspective view illustrating the sensor unit and pipette devices.

Passage apertures 16b are formed in the sealing structure 16, and positioned at the first and second orifices 20a and 20b of the flow channels 20 and 21, and the first and second orifices 21a and 21b of the flow channel 21, for entry of an end of the pipette devices (See FIG. 2). The passage apertures 16b have a funnel shape with a decreasing diameter for introducing liquid ejected by the pipette toward the flow channels 20 and 21. In engaging the flow cell devices 12 with the prism 14, a lower face of the passage apertures 16b is connectable with each of the first and second orifices 20a and 20b and the first and second orifices 21a and 21b of the flow channels 20 and 21 for flow of fluid.

Note that an RFID tag (radio frequency identification tag) as a non-contact IC memory may be used with and secured to any one elements in the sensor unit 10 such as the prism 14 and the sealing structure 16. An ID number for the sensor unit 10 is stored in the RFID tag of the read only type. The ID number is read out at each time before operation of one of sequential processes, so the sensor unit 10 can be identified. It is possible to prevent failure or errors in simultaneous immobilization and assay of plural sensor units, such as erroneous introduction of analyte fluid, misreading of results of measurement. Also, the RFID tag may be a writeable type. Information can be written to the RFID tag in sequential processes, such as types of immobilized ligand, date of immobilization, types of analytes used in the reaction, and the like.

In FIG. 2, an SPR (surface plasmon resonance) assay apparatus 30 as a flow cell system for assay in utilizing attenuated total reflection. The assay apparatus 30 includes an optical assay unit 32 and a fluid dispensing head or fluid dispenser 34. The optical assay unit 32 outputs an SPR signal by sensing reaction and interaction of sample on the thin film 25 of the sensor unit 10. The fluid dispenser 34 dispenses fluid to each of the flow channels 20 and 21 in the sensor unit 10. A controller (not shown) controls those element.

The optical assay unit 32 includes light sources 40 and 41 and a photo detector 42. The light sources 40 and 41 apply light to the sensor unit 10 to satisfy the total reflection condition. The photo detector 42 receives the light reflected by the sensor unit 10 in the total reflection, and converts the light into a photoelectric signal. An assay stage 44 supports the light sources 40 and 41 and the photo detector 42 in a fixed manner. An example of the assay stage 44 is a support in a trapezoidal shape, and sets the light sources 40 and 41 and the photo detector 42 to satisfy the total reflection condition. The assay stage 44 supports the sensor unit 10 in a removable manner to position the sensor unit 10 in light paths of the light sources 40 and 41.

Figure 3:
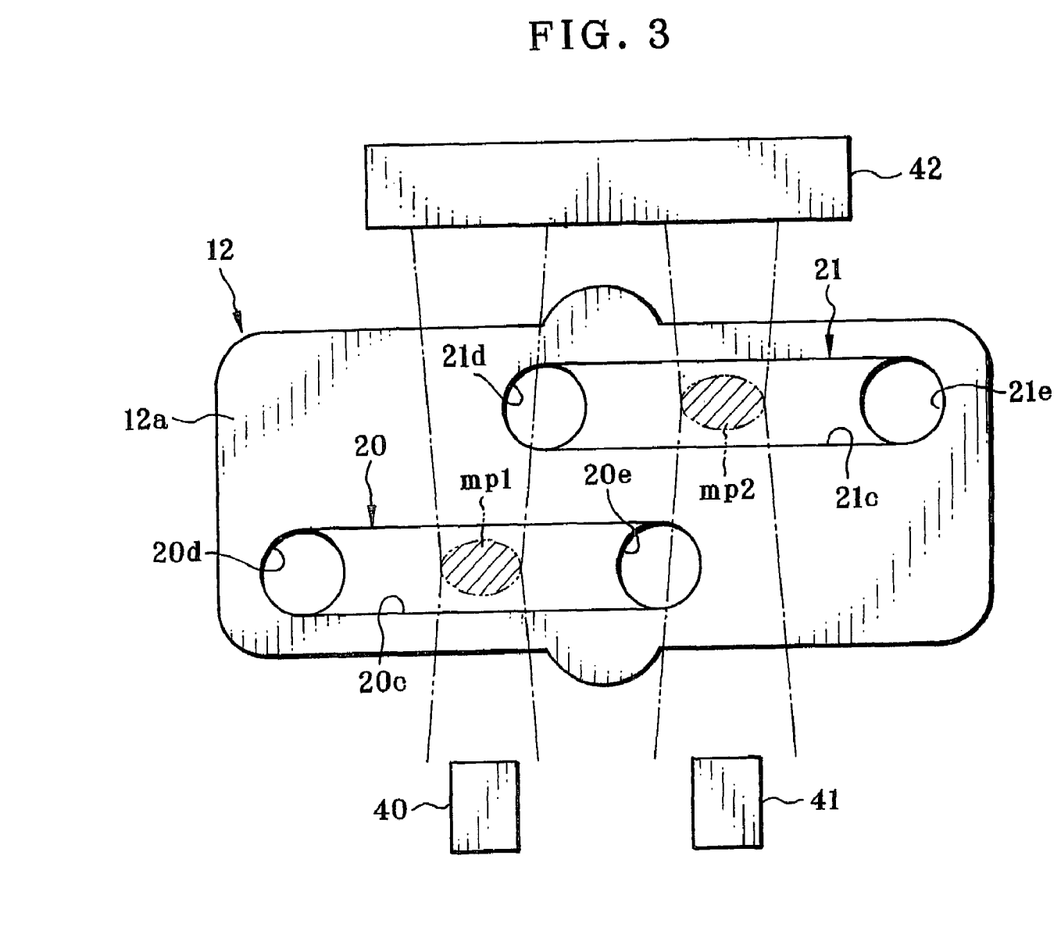
FIG. 3 is an explanatory view in plan, illustrating a flow cell device.

The light sources 40 and 41 are combined with respectively the flow channels 20 and 21 of the sensor unit 10, and apply light to the prism 14 at various incident angles satisfying the total reflection condition. Each of the light sources 40 and 41 includes a light source element (not shown) and an optical system, which includes a condensing lens, a diffusing plate and a polarizer. A position and angle of installation of those elements are so determined that an angle of incidence of the light satisfies the condition of the above total reflection. As illustrated in FIG. 3, the light condensed by the prism 14 is caused to enter the middle of the fluid passageways 20c and 21c. In FIG. 3, the flow cell devices 12 is viewed from a lower side.

Sample fluid is dispensed and introduced to the flow channels 20 and 21 for contact with the thin film 25 at the fluid passageways 20c and 21c. Changes in the refractive index occurs upon immobilizing the ligand on the linker film 26 or by interaction between the ligand and analyte. The optical assay unit 32 condenses light from the light sources 40 and 41 at a point in the interface outside the prism 14 and opposed to the middle of the fluid passageways 20c and 21c. The photo detector 42 receives the reflected light, and checks changes in the refractive index. Let a first measuring point mp1 be a point of condensation of light from the light source 40 in the interface outside the prism 14, being indicated as a hatched portion. Let a second measuring point mp1 be a point of condensation of light from the light source 41 in the interface outside the prism 14.

It is likely that contamination may occur upon introduction of fluids in a changeover manner in the flow channels 20 and 21, because aspiration for removal cannot be complete and may cause residue of the first fluid. A degree of contamination is referred to a ratio of substitution, which is changeable between the wall position and a position at the center of the flow channels 20 and 21, and between a point near to a first orifice for dispensation and a second orifice for the aspiration and removal. The measuring points mp1 and mp2 according to the light sources 40 and 41 are defined at the center of respectively the fluid passageways 20c and 21c, so as to suppress a great difference in the ratio of substitution irrespective of selection of the orifices for the introduction of fluid. Errors in the assay due to changes in the ratio of substitution can be canceled by means of analysis according to the measuring and reference regions. In the present embodiment, the measuring points mp1 and mp2 are disposed at the center of respectively the fluid passageways 20c and 21c. The path length of the flow from the orifices is equal irrespective of which orifice fluid is introduced in. A difference in the ratio of substitution between the measuring points mp1 and mp2 is small, so errors in the assay due to the ratio of substitution can be reduced reliably in the course of the analysis.

Examples of the light sources 40 and 41 include a light emitting diode (LED), laser diode (LD), super luminescent diode (SLD), and other light emitting element. A single element selected from those is used as the light sources 40 and 41, to illuminate the measuring points mp1 and mp2. There is a diffusing plate which diffuses light from the light sources 40 and 41, and suppresses onset of irregularity in the light amount. A polarizer allows only p-polarized light to pass, the p-polarized light creating the surface plasmon resonance. Note that no polarizer is required if directions of rays emitted by the light sources 40 and 41, for example an LD, are kept equal. However, a polarizer may be combined with the light sources 40 and 41 of a type of which directions of emitted rays are kept equal. Directions of rays in polarization are changed to an unequal state by the passage through the diffusing plate. For this structure, the polarizer can be utilized to set equal the directions of the rays. The light obtained after the diffusion and polarization is condensed by a condensing lens, and directed to the prism 14. It is possible to travel rays with various angles of incidence toward the interface without irregularity in the intensity.

Although the light sources 40 and 41 are used in the invention, a single light source can be used, and associated with a device for splitting light from the light source into two light paths to illuminate the measuring points mp1 and mp2. Also, the number of the light sources 40 and 41 may be three or more, so that the measuring points mp1 and mp2 of the three flow cell devices 12 can be illuminated for assay simultaneously. Splitting of the light may be used in combination of the light sources 40 and 41 of the modified number.

An example of the photo detector 42 is a CCD area sensor or an array of photo diodes. Light, upon entry in the prism 14 through a first lateral surface, passes through the prism 14 and condensed on the interface between the prism 14 and the thin film 25. Then the light is reflected by the interface and exits from the prism 14 through a second lateral surface. As light of various angles enters the prism 14, the light is reflected by the interface outside the prism 14 at various angles of reflection according to the angles of incidence. The photo detector 42 receives the reflected light, converts the reflected light to output an SPR signal of levels according to the strength of the light. Also, the photo detector 42 receives reflected light from a first measuring point mp1 and a second measuring point mp2, to output the SPR signal. Consequently, the optical assay unit 32 assays for two output channels by use of the light sources 40 and 41 and the photo detector 42.

If a CCD area sensor is used as the photo detector 42, reflected light of the dual channels received at the same time can be recognized as SPR outputs of the measuring points mp1 and mp2 by the image processing. However, such a method according to the image processing might be too difficult. Alternatively, signals of the signal channels can be received by scheduling a difference in the incidence for a very small period of time of the incidence between the measuring points mp1 and mp2. An example of scheduling a difference in the incidence is a use of a disk disposed on a light path and having two holes positioned at 180 degrees of a rotational angle. The disk is rotated to shift the time sequence between the signal channels. The holes are disposed at a difference of the radius from the rotational center in association with the interval between the measuring points mp1 and mp2. When a first one of the holes enters the light path, illuminating light travels to the measuring point mp1. When a second one of the holes enters the light path, the light travels to the measuring point mp2. Thus, the incidence of light can be scheduled between the signal channels. Note that, although the photo detector 42 is single, two separate photo detectors may be used for the measuring points mp1 and mp2.

First and second pipette devices 46*a* and 46*b* are provided in the fluid dispenser 34, and access the first and second orifices 20*a* and 20*b* of the flow channel 20 and the first and second orifices 21*a* and 21*b* of the flow channel 21. A pump, for example a syringe pump, is connected with each of the first and second pipette devices 46*a* and 46*b*, and is driven to control dispensation and aspiration of fluids. A dispenser shifting mechanism 36 is connected with the fluid dispenser 34. The dispenser shifting mechanism 36 is a moving device and may include a conveyor belt, pulleys, a carriage and a motor. A controller controls the dispenser shifting mechanism 36 to move the fluid dispenser 34 in a three dimensional manner.

The first and second pipette devices 46*a* and 46*b* on the fluid dispenser 34 has tubular shape with a deceasing diameter, and arranged with an interval set for the interval between the first and second orifices 20*a* and 20*b* and the first and second orifices 21*a* and 21*b*. Pipette tips are ends of the first and second pipette devices 46*a* and 46*b* and fitted removably. As the pipette tips contact fluid directly, the first and second pipette devices 46*a* and 46*b* are exchanged at each time of dispensation to prevent contamination between plural fluids with the first and second pipette devices 46*a* and 46*b*. A pipette tip storage (not shown) is installed in the assay apparatus 30 for storing numerous pipette tips. To exchange pipette tips, the dispenser shifting mechanism 36 is driven for the fluid dispenser 34 to access the pipette tip storage.

A multi well plate 38 or reservoir is installed in the assay apparatus 30 and stores various fluids for dispensation to the flow channels 20 and 21, such as ligand fluid, analyte fluid, washing liquid, buffer liquid and the like. The dispenser shifting mechanism 36 moves the fluid dispenser 34 for access to the multi well plate 38 and the sensor unit 10 set on the assay stage 44.

Figure 4A:
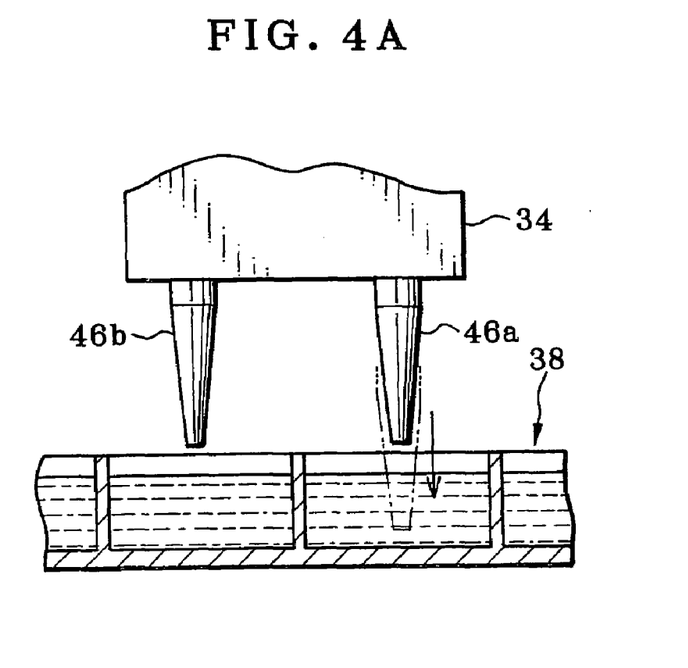
FIG. 4A is an explanatory view in cross section, illustrating a multi well plate with the pipette devices.

A pipette advancing mechanism (not shown) is incorporated in the fluid dispenser 34 for advancing the first and second pipette devices 46*a* and 46*b* discretely. The fluid dispenser 34 accesses the multi well plate 38, and causes only one of pipette devices to advance for aspirating fluid as illustrated in FIG. 4A, to enter the fluid within one of the wells. Thus, it is possible to prevent a second one of the pipette devices from entry in the fluid within a well and from contacting an unintended fluid. Note that a plurality of fluids are stored in wells in the multi well plate 38 in a distinct manner. However, a plurality of multi well plates can be used and can be associated with respectively the fluids.

Figure 4B:
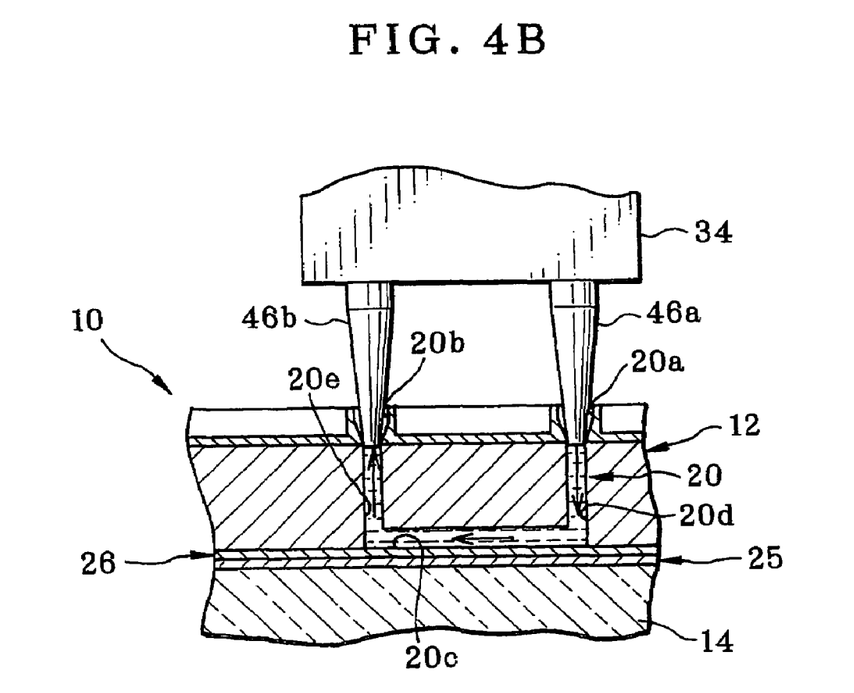
FIG. 4B is an explanatory view in cross section, illustrating the sensor unit with the pipette devices.

For dispensation of fluid from the fluid dispenser 34 to the flow channels 20 and 21, the first and second pipette devices 46*a* and 46*b* are inserted into the first and second orifices 20*a* and 20*b* of the flow channel 20 or the first and second orifices 21*a* and 21*b* of the flow channel 21. See FIG. 4B. A first one of the pipette devices is caused by the fluid dispenser 34 to dispense fluid. A second one of the pipette devices is caused to aspirate air or fluid from the flow channels 20 and 21. Thus, the fluid dispenser 34 causes fluid to flow in the flow channels 20 and 21 for exchange.

Figure 5:
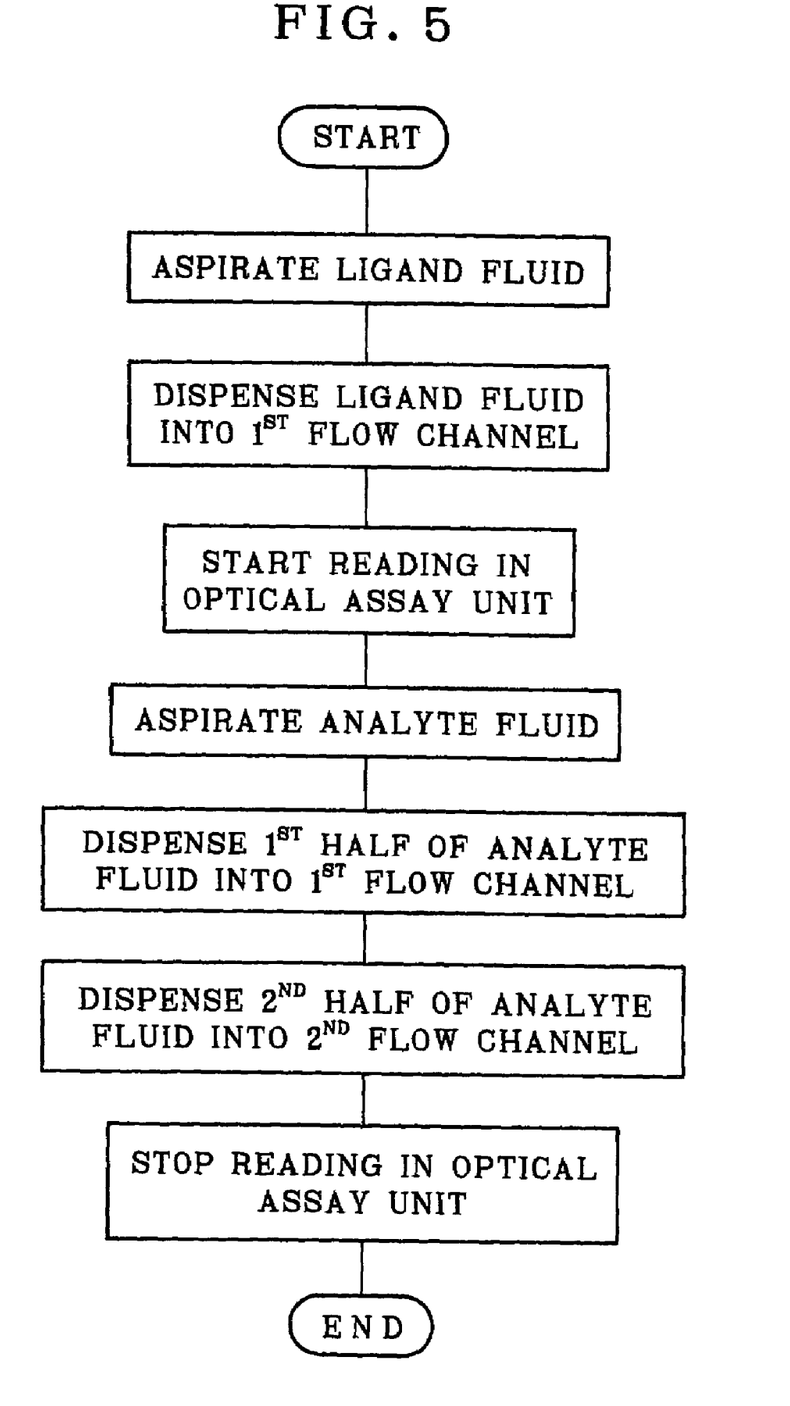
FIG. 5 is a flow chart illustrating dispensation of fluids into a flow channel.

The operation of the assay apparatus 30 is described with reference to FIG. 5. At first the sensor unit 10 is set on the assay stage for measuring interaction between ligand and analyte. The sensor unit 10 is positioned so as to position one of the flow cell devices 12 in a light path from the light sources 40 and 41. The assay apparatus 30 operates for three steps of ligand immobilizing flow, assay and data analysis for measuring the interaction. In the ligand immobilizing flow step, ligand flows and is immobilized in the sensor unit 10. In the assay step, analyte is caused to contact immobilized ligand, to output an SPR signal. In the data analysis, the SPR signal is analyzed.

After the sensor unit 10 is set, the assay apparatus 30 starts ligand immobilizing flow upon receipt of start of the ligand immobilizing flow by a manual input of a user. In response, a controller of the assay apparatus 30 drives the dispenser shifting mechanism 36 to shift the fluid dispenser 34 to the multi well plate 38. The controller drives an advancing mechanism to advance the first pipette device 46*a*, which enters one of the wells storing ligand fluid. The first pipette device 46*a* aspirates the ligand fluid at a predetermined amount from the well. Then the controller moves the fluid dispenser 34 with the acquired ligand fluid to the sensor unit 10, and inserts the first and second pipette devices 46*a* and 46*b* into the first and second orifices 20*a* and 20*b* of the flow channel 20 for measurement.

The controller drives the first and second pipette devices 46a and 46b to cause the first pipette device 46a to dispense and the second pipette device 46b to aspirate, so ligand fluid is introduced to the flow channel 20. The ligand is immobilized on the linker film 26 inside the flow channel 20, to complete the immobilization. Note that it is possible before introducing ligand fluid in the flow channel 20 to wash the flow channel 20 or activate the linker film 26. Until the immobilization, the ligand fluid in the flow channel 20 may be left to stand in a stationary state. However, the ligand fluid can be preferably stirred or turbulently flowed for ensured fluidity in the flow channel 20 by alternate driving of the first and second pipette devices 46a and 46b for dispensation and aspiration. The stirring or turbulent flow can promote binding of the ligand with the linker film 26, to raise an immobilized amount of the ligand.

The assay apparatus 30 with the ligand immobilized on the linker film 26 keeps the sensor unit 10 conditioned at suitable temperature or other states of environment, and starts the ligand immobilizing flow upon entry of an input of start of measurement by a user. In response, the controller starts reading data in the optical system with the light sources 40 and 41 and the photo detector 42. Also, the dispenser shifting mechanism 36 is driven to shift the fluid dispenser 34 to the multi well plate 38. An advancing mechanism is caused by the controller to advance the first pipette device 46a, which aspirates analyte fluid at a predetermined amount from the multi well plate 38.

With the analyte fluid in the first pipette device 46a, the fluid dispenser 34 is shifted to the sensor unit 10, and sets the first and second pipette devices 46a and 46b in the first and second orifices 20a and 20b of the flow channel 20. The controller drives the first and second pipette devices 46a and 46b to cause the first pipette device 46a to dispense and the second pipette device 46b to aspirate, so analyte fluid is introduced to the flow channel 20. Approximately a half of the stored analyte fluid in the first pipette device 46a is introduced in the flow channel 20. After this, the fluid dispenser 34 is shifted to set the first and second pipette devices 46a and 46b in the first and second orifices 21a and 21b of the flow channel 21. A remaining half of the stored analyte fluid in the first pipette device 46a is introduced in the flow channel 21. Note that a volume of each of the first and second pipette devices 46a and 46b is preferably two times as much as a volume of the flow channel 20 or 21.

Ligand is immobilized on the linker film 26 positioned in the flow channel 20, and starts reaction with the analyte upon dispensation of analyte fluid. The photo detector 42 outputs an SPR signal as measuring signal according to the reflected light from the measuring point mp1. In contrast, no ligand is immobilized on the linker film 26 positioned in the flow channel 21. The analyte remains free from reaction. The photo detector 42 outputs an SPR signal as reference signal according to the reflected light from the measuring point mp2.

The signals being output, the assay apparatus 30 interrupts data reading by means of the light sources 40 and 41 and the photo detector 42, to terminate the assay. Reading of data in a photo detector starts upon initially introducing liquid buffer in the flow channels 20 and 21. The reading is continued until the introduction of the liquid buffer at the second time after entry of analyte fluid. It is possible not only to detect the reference level that is a base line, but to assay the interaction or reaction between the analyte and the ligand, and to measure a signal until dissociation between the analyte and ligand in response to introduction of the liquid buffer.

After the assay, the assay apparatus 30 subtracts a level of the reference signal from a level of the measuring signal, to obtain measured data, and analyzes the interaction between the ligand and analyte according to the measured data. Fluids are caused to flow in the flow channels 20 and 21 that are distinct from one another, to obtain the measuring signal and the reference signal from the linker film 26 of which the surface is common. Thus, no difference in the non specific adsorption will occur between the signals. Influence of non specific adsorption can be suppressed by the analysis. Also, the flow channels 20 and 21 are positioned to overlap one portion of the fluid passageways 20c and 21c in the flow cell longitudinal direction of the flow cell body 12a. This is effective in positioning the flow channels 20 and 21 in a concentrated manner. The sensor unit 10 can be free from having an enlarged size despite the separated use of the flow channels for the measuring signal and reference signal. Throughput of the assay can be high.

The measuring points mp1 and mp2 are defined at the center of respectively the fluid passageways 20c and 21c. The path length of the flow from the orifices is equal irrespective of which orifice fluid is used for introduction. A difference in the ratio of substitution between the measuring points mp1 and mp2 can be set small. Errors in the assay due to the ratio of substitution can be reduced reliably. According to the known technique in contrast, fluids of considerable amounts have been used for the purpose of suppressing a difference in the ratio of substitution. However, it is possible in the invention to suppress errors in the assay reliably in the analysis. This is effective in saving amounts of the fluids.

Figure 6:
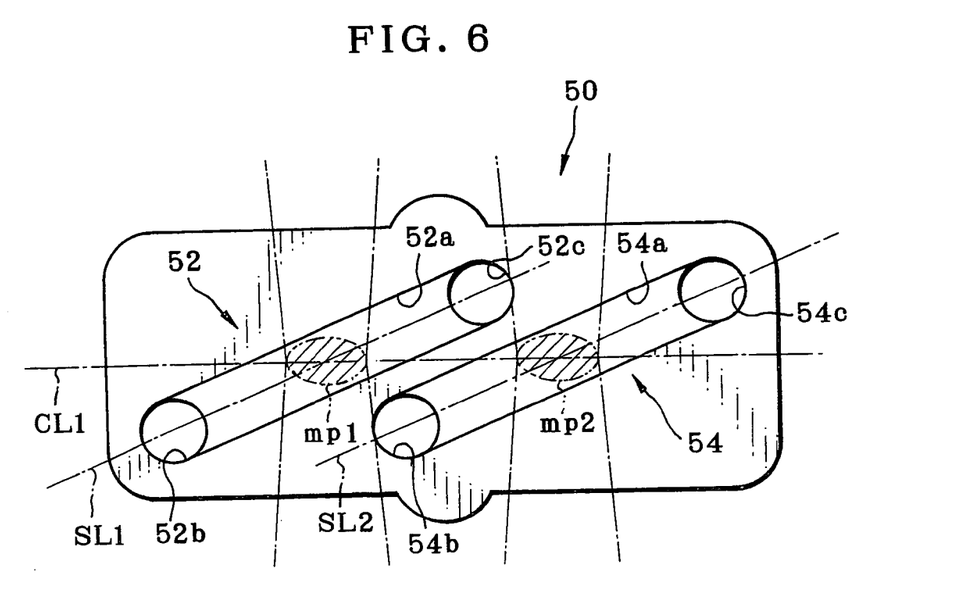
FIG. 6 is an explanatory view in plan, illustrating one preferred flow cell device with inclined fluid passageways.

Other preferred embodiments of flow channels are hereinafter described. In FIG. 6, a flow cell device 50 of the invention has flow channels 52 and 54. A fluid passageway 52a is a middle of the flow channel 52. End cavities 52b and 52c as ends of the flow channel 52 are connected with the fluid passageway 52a. A fluid passageway 54a is a middle of the flow channel 54. End cavities 54b and 54c as ends of the flow channel 54 are connected with the fluid passageway 54a. The fluid passageways 52a and 54a extend straight. A line SL1 straight along the fluid passageway 52a intersects with the central line or reference straight line CL1 with an inclination. A line SL2 straight along the fluid passageway 54a intersects with the reference line CL1 with an inclination.

In the embodiment of FIG. 3, the measuring points mp1 and mp2 are offset in the width direction because the fluid passageways 20c and 21c extend in the flow cell longitudinal direction. This causes complexity in the optical system, as the two light sources 40 and 41 should be used, or as a single light source should be shifted at an offset amount. In contrast, in FIG. 6, the measuring points mp1 and mp2 are arranged on the central line or reference straight line CL1. This is effective in simplifying the optical system, because of a single light source. In the flow channels 52 and 54, first and second intersection points are defined by the reference line CL1 and the straight line SL1 and by the reference line CL1 and the straight line SL2. It is preferable that a path length between the first intersection point and any of the orifices 20a and 20b is equal to a path length between the second intersection point and any of the orifices 21a and 21b. This can keep the sensor unit 10 oriented without an inclination, because force exerted by the insertion of the first and second pipette devices 46a and 46b can be exerted equally between the right and left sides.

Figure 7:
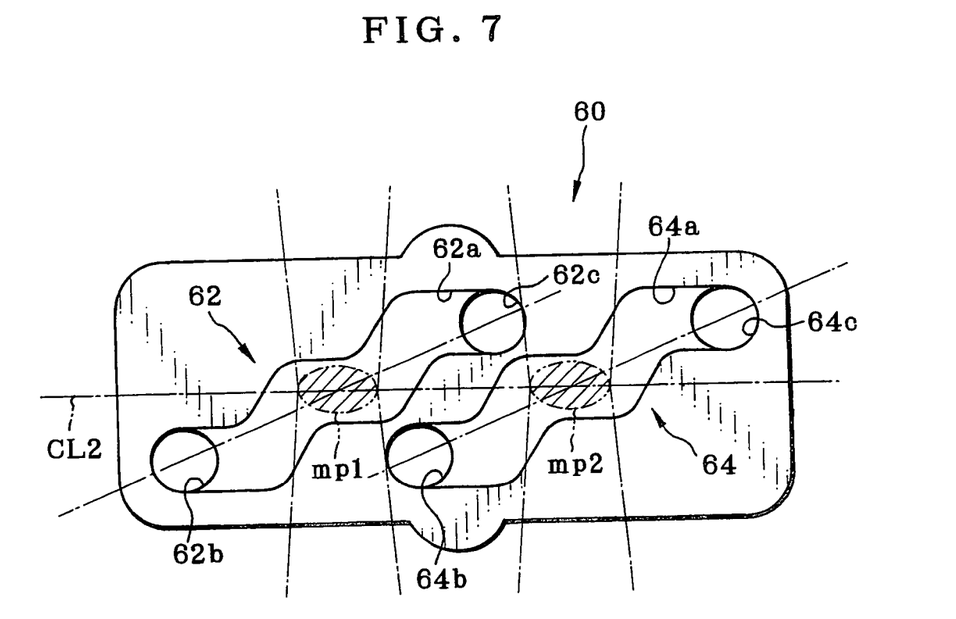
FIG. 7 is an explanatory view in plan, illustrating one preferred flow cell device with fluid passageways in a wave shaped bent form.

In FIG. 7, another preferred flow cell device 60 has flow channels 62 and 64 of which fluid passageways 62a and 64a are bent horizontally in a smooth wave shape. In FIG. 6, the fluid passageways 52a and 54a of the flow channels 52 and 54 intersect with the central line or reference straight line CL1. In FIG. 7, in contrast, the fluid passageways 62a and 64a of the flow channels 62 and 64 extend along the reference line CL2 at points of intersecting with the reference line CL2. The measuring points mp1 and mp2 are offset from positions on inner surfaces of the fluid passageways 62a and 64a where substitution of fluid is slow. Thus, the assay can be more precise by preventing errors in the assay due to the substitution.

Figure 8:
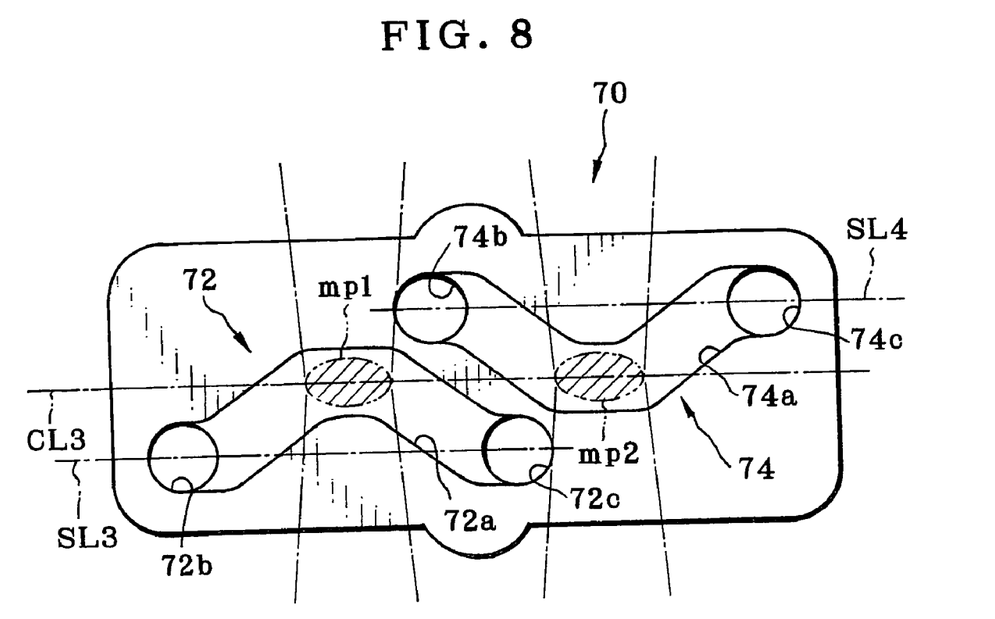
FIG. 8 is an explanatory view in plan, illustrating one preferred flow cell device with fluid passageways in a bent form with an obtuse angle.

In FIG. 8, another preferred flow cell device 70 is illustrated. A flow channel 72 in the flow cell device 70 includes a fluid passageway 72a and end cavities 72b and 72c at its ends. A flow channel 74 in the flow cell device 70 includes a fluid passageway 74a and end cavities 74b and 74c at its ends. Let a straight line SL3 be a line passing ends of the fluid passageway 72a. Let a straight line SL4 be a line passing ends of the fluid passageway 74a. The straight lines SL3 and SL4 are parallel with the central line or reference straight line CL3 of the flow cell device 70 in the flow cell longitudinal direction. The flow channels 72 and 74 are opposed to one another with respect to the reference line CL3. The fluid passageway 72a and 74a are bent at an obtuse angle in the V shape, and intersect with the reference line CL3.

In FIGS. 6 and 7, each of the fluid passageways extends with inclinations from the central line. The construction of the flow cell system may be complicated owing to positioning of the first and second pipette devices 46a and 46b or the fluid dispenser 34 by considering the inclinations for the dispensation. In FIG. 8, however, the lines SL3 and SL4 passing ends of respectively the fluid passageways 72a and 74a extend along the central line or reference straight line CL3. This is advantageous because no complicated structure for flow is required. Note that, in the flow cell device 70, the fluid passageways 72a and 74a can preferably extend along the reference line CL at the portion intersecting the reference line CL3 of the flow cell device 70 in a similar manner to the embodiment of FIG. 7, the portion corresponding to the measuring points mp1 and mp2.

Figure 9:
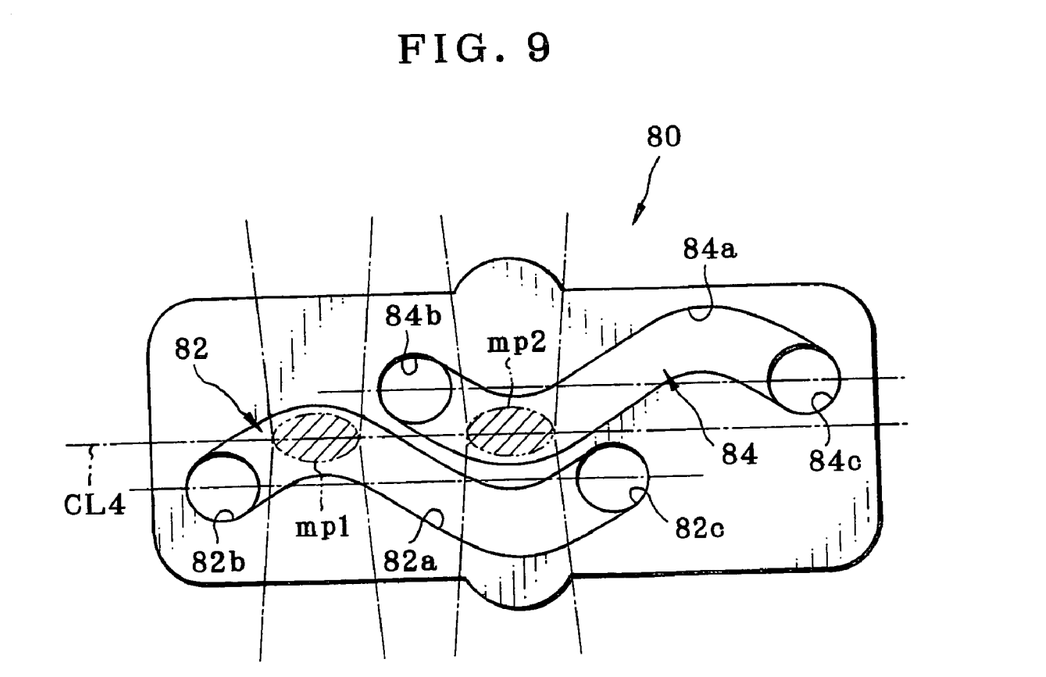
FIG. 9 is an explanatory view in plan, illustrating one preferred flow cell device with S shaped fluid passageways.

In FIG. 9, one preferred flow cell device 80 is illustrated. A flow channel 82 in the flow cell device 80 includes a fluid passageway 82a in an S shape and end cavities 82b and 82c at its ends. A flow channel 84 in the flow cell device 80 includes a fluid passageway 84a in an S shape and end cavities 84b and 84c at its ends. The end cavities 82b and 82c and the end cavities 84b and 84c are determined very near to the central line or reference straight line CL4. If the central line is parallel with a straight line passing ends of a fluid passageway, force with an inclination is likely to occur with respect to the central line upon insertion of the first and second pipette devices 46a and 46b in orifices. However, in the embodiment of FIG. 9, the flow channels 82 and 84 are formed and disposed very near to the reference line CL4. This is effective in reducing force with an inclination upon insertion of the first and second pipette devices 46a and 46b, to prevent errors in the assay due to an inclination of the sensor unit 10.

Figure 10:
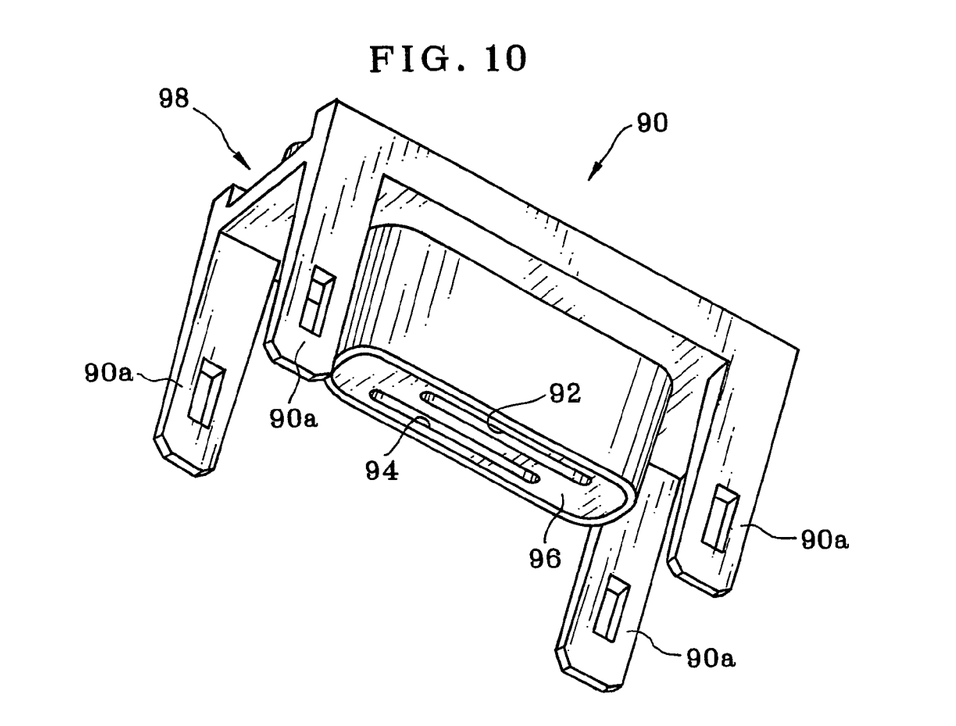
FIG. 10 is a bottom perspective view illustrating another preferred flow cell device including an elastic flexible layer.
Figure 11:
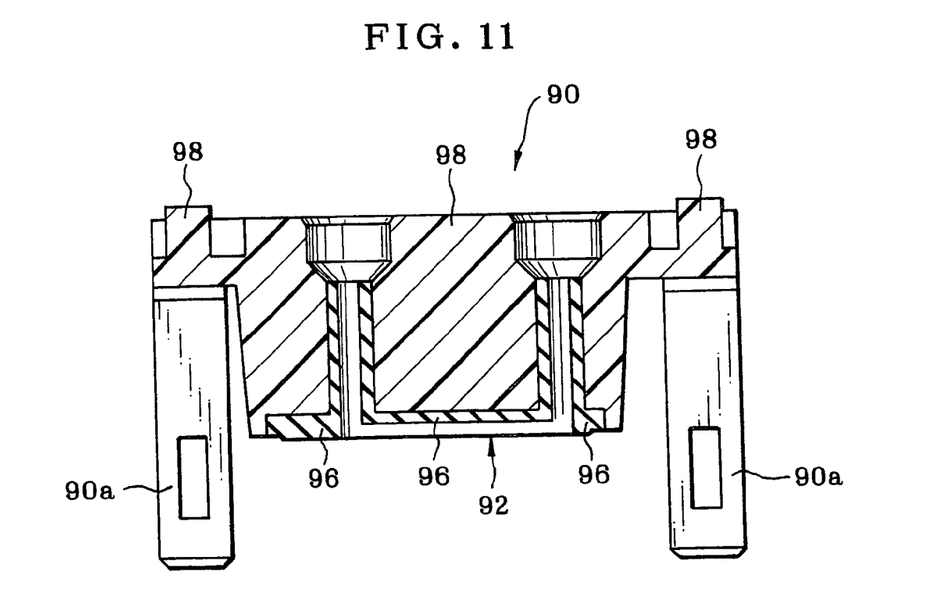
FIG. 11 is a cross section illustrating the same as FIG. 10.

In FIGS. 10 and 11, one preferred flow cell device 90 has a feature without the above sealing structure 16 for fixation. A retention portion 90a of the flow cell device 90 is engageable with the retention claws 14a of the prism 14, so the flow cell device 90 itself can be connected with the prism 14. First and second flow channels 92 and 94 formed in the flow cell device 90 can be positioned relative to the prism 14.

The flow cell device 90 is constituted by an elastic flexible layer or part 96 as sealant and a hard part 98 or flow cell body. The elastic flexible layer 96 extends in the entirety of the inner surface of the first and second flow channels 92 and 94, and has smaller hardness than the hard part 98. The hard part 98 and the elastic flexible layer 96 are formed by a method of double molding or dual molding in which two materials are combined within a mold for forming.

The elastic flexible layer or part 96 protrudes slightly from a lower face of the hard part 98 or flow cell body, and elastically seals a position with the thin film 25 by elastic deformation upon attachment on the prism 14, to keep the lower opening of the first and second flow channels 92 and 94 closed in a fluid tight manner. A preferable thickness of the elastic flexible layer 96 is equal to or more than 0.1 mm and equal to or less than 1.0 mm. Should the thickness be less than 0.1 mm, an effect of the fluid tight sealing cannot obtained due to small deformation of the elastic flexible layer 96. Should the thickness be more than 1.0 mm, excessive offsetting in the position will be caused by the deformation of the elastic flexible layer 96. Note that a preferable amount of lower protrusion of the elastic flexible layer 96 is approximately 0.1 mm in consideration of elasticity.

The elastic flexible layer or part 96 contacts the sample fluid flowing in the first and second flow channels 92 and 94 because overlaid on the inner wall of the first and second flow channels 92 and 94. Adsorption of samples contained in the sample fluid should be prevented in view of the required contact of the elastic flexible layer 96 with the sample fluid. Thus, it is preferable that the material characteristically has a small non-specific adsorption. Examples of the materials for the elastic flexible layer 96 on the hard part 98 include elastic resins having small non-specific adsorption, such as amorphous polyolefin elastomer. Examples of the hard materials for the hard part 98 include crystalline polyolefin, such as polypropylene.

Note that a region of the elastic flexible layer or part 96 can constitute the at least a periphery of fluid passageways of the first and second flow channels 92 and 94. However, the elastic flexible layer 96 according to the embodiment extends in the entirety of the inner surface of the first and second flow channels 92 and 94, and is effective in suppressing failure in dispensation on borderlines or the like. Also, an area defined by forming can be large, and can improve moldability. The elastic flexible layer 96 can be prevented from dropping out of the hard part 98 or flow cell body in a formed state.

Although the assay apparatus 30 is single in the embodiments, plural apparatuses may be used discretely for the ligand immobilizing flow, assay and data analysis. This is effective in raising efficiency in the assay, because a great number of the sensor units 10 can be treated simultaneously and rapidly one after another.

In the above embodiment, a dielectric medium is the prism 14. However, a dielectric medium used in the invention may be a panel of an optical glass, a panel of an optical plastic material, and a composite structure including a prism, panels of any of those, and index-matching oil with which the prism and panels are fitted.

In addition to the SPR sensor, an assay sensor unit according to the invention can be other sensor in utilizing attenuated total reflection. One example of sensor unit according to utilizing the attenuated total reflection is a leaky mode sensor. The leaky mode sensor includes a dielectric medium, a cladding layer overlaid on the dielectric medium, and an optical waveguide layer overlaid on the cladding layer, those layers constituting a thin film. A first surface of the thin film is a sensing surface on the optical waveguide layer. A second surface of the thin film is a metal/dielectric interface on the cladding layer. When light becomes incident on the metal/dielectric interface to satisfy the condition of the total reflection, part of the light passes through the cladding layer, and enters the optical waveguide layer. A guided mode to propagate light is excited responsively in the optical waveguide layer, to attenuate the reflected light on the metal/dielectric interface. An angle of the incidence at which the guided mode is excited is changeable according to the refractive index of the medium positioned on the sensing surface. This is similar to the characteristic of the resonance angle of the SPR sensor. The attenuation of the reflected light is detected, so that it is possible to measure the interaction on the sensing surface.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. A flow cell device comprising:
    a flow cell body, having a lower surface, and disposed in contact of said lower surface with a sensing surface for detecting reaction of sample;
    at least two flow channels, formed in said flow cell body, for flow of said sample;
    each of said flow channels including a fluid passageway, formed in said lower surface, for flow of said sample in contact with said sensing surface, and two end cavities, formed in an upper surface of said flow cell body and open therein, to extend from ends of said fluid passageway;
    at least one flow channel set constituting said at least two flow channels, said flow channels being arranged adjacent to one another as viewed in a direction of said flow, disposed to extend in said direction of said flow, fluid passageways of said flow channels being overlapped partially on one another in a predetermined direction of said flow cell body;
    wherein each of said fluid passageways extends to intersect with a reference straight line extending in said predetermined direction, and wherein a measurement point of each of said fluid passageways is disposed at a point on the reference straight line.

2. The flow cell device as defined in claim 1, wherein said reference straight line is a flow cell central line defined by a shape of said flow cell body.

3. The flow cell device as defined in claim 2, wherein said fluid passageway is so disposed that a straight line that passes through the ends thereof is inclined with said reference straight line.

4. The flow cell device as defined in claim 3, wherein said fluid passageway is so disposed that said end cavities are disposed at an equal path length from intersection point between said straight line and said reference straight line.

5. The flow cell device as defined in claim 3, wherein said fluid passageway is formed to extend substantially linearly.

6. The flow cell device as defined in claim 3, wherein said fluid passageway is formed to extend in a wave shaped bent form.

7. The flow cell device as defined in claim 2, wherein said fluid passageway is so disposed that a straight line that passes through the ends thereof extends along with said reference straight line.

8. The flow cell device as defined in claim 7, wherein said fluid passageway is in a bent form toward a reference straight line, and said two flow channels are opposed to one another with respect to said reference straight line.

9. The flow cell device as defined in claim 7, wherein said fluid passageway is formed to extend in an S shaped bent form.

10. The flow cell device as defined in claim 9, wherein said two flow channels are opposed to one another with respect to said reference straight line.

11. The flow cell device as defined in claim 1, further comprising a retention portion, formed to project from said flow cell body, engageable with a support having said sensing surface, for keeping said sensing surface in contact with said lower surface.

12. The flow cell device as defined in claim 1, wherein said flow cell body includes:
    a hard part; and
    an elastic flexible part, formed together with said hard part according to dual molding, having a smaller hardness than said hard part, for constituting at least an edge of said fluid passageway.

13. A sensor unit, having a dielectric medium overlaid with a thin film for attenuating reflected illuminating light upon application of said illuminating light to satisfy a total reflection condition, and at least one flow cell device disposed to contact said dielectric medium, for causing sample to flow to a sensing surface on said thin film, wherein when said sample contacts said sensing surface, an incidence angle of said illuminating light of occurrence of attenuation is changed according to reaction of said sample, said sensor unit comprising:
    said flow cell device including:
        a flow cell body, having a lower surface, and disposed in contact of said lower surface with said sensing surface;
        at least two flow channels, formed in said flow cell body, for flow of said sample;
        each of said flow channels including a fluid passageway, formed in said lower surface, for flow of said sample in contact with said sensing surface, and two end cavities, formed in an upper surface of said flow cell body and open therein, to extend from ends of said fluid passageway;
    said flow cell device including at least one flow channel set constituting said at least two flow channels, said flow channels being arranged adjacent to one another as viewed in a direction of said flow, disposed to extend in said direction of said flow, fluid passageways of said flow channels being overlapped partially on one another in a predetermined direction of said flow cell body;
    wherein each of said fluid passageways extends to intersect with a reference straight line extending in said predetermined direction, and wherein a measurement point of each of said fluid passageways is disposed at a point on the reference straight line.

14. The sensor unit as defined in claim 13, wherein said flow channels in said flow channel set include:
    a first flow channel adapted to generating a measuring signal of information of detecting said reaction; and
    a second flow channel adapted to generating a reference signal for analysis of said measuring signal.

15. The sensor unit as defined in claim 13, wherein said at least one flow cell device is plural flow cell devices arranged in a flow cell array.

16. An assay apparatus for an assay utilizing attenuated total reflection, comprising:
    an assay stage for supporting a removable sensor unit,
    a light source for applying illuminating light to a thin film of said sensor unit to satisfy a total reflection condition, and
    a photo detector for receiving said illuminating light reflected by said thin film and for conversion into an electric signal, wherein:
    said sensor unit comprises a dielectric medium overlaid with said thin film for attenuating reflected illuminating light upon application of said illuminating light to satisfy a total reflection condition, and at least one flow cell device disposed to contact said dielectric medium, for causing sample to flow to a sensing surface on said thin film, wherein when said sample contacts said sensing surface, an incidence angle of said illuminating light of occurrence of attenuation is changed according to reaction of said sample; and said flow cell device comprises:
- a flow cell body, having a lower surface, and disposed in contact of said lower surface with said sensing surface;
- at least two flow channels, formed in said flow cell body, for flow of said sample;
- each of said flow channels including a fluid passageway, formed in said lower surface, for flow of said sample in contact with said sensing surface, and two end cavities, formed in an upper surface of said flow cell body and open therein, to extend from ends of said fluid passageway;
- said flow cell device including at least one flow channel set for constituting said at least two flow channels, said flow channels being arranged adjacent to one another as viewed in a direction of said flow, disposed to extend in said direction of said flow, fluid passageways of said flow channels being overlapped partially on one another in a predetermined direction of said flow cell body;
- wherein each of said fluid passageways extends to intersect with a reference straight line extending in said predetermined direction, and wherein a measurement point of each of said fluid passageways is disposed at a point on the reference straight line.

17. The assay apparatus as defined in claim 16, wherein there are two paths where said light source applies said illuminating light to said thin film, and said illuminating light travels to a measuring point defined in said fluid passageway;
said measuring point is disposed at a first path length from a first end cavity for dispensing said sample among said end cavities, said first path length being equal in each of said at least two flow channels.

18. The assay apparatus as defined in claim 17, wherein said measuring point is disposed at a second path length from a second end cavity for exiting said sample among said end cavities, and said second path length is equal to said first path length.

* * * * *